United States Patent [19]

Beschke et al.

[11] 4,447,614

[45] May 8, 1984

[54] PROCESS FOR THE PURIFICATION OF NICOTINIC ACID AMIDE

[75] Inventors: Helmut Beschke, Hanau; Franz-Ludwig Dahm, Alzenau; Heinz Friedrich; Günter Prescher, both of Hanau, all of Fed. Rep. of Germany

[73] Assignee: Degussa Aktiengesellschaft, Fed. Rep. of Germany

[21] Appl. No.: 288,187

[22] Filed: Jul. 29, 1981

[30] Foreign Application Priority Data

Jul. 30, 1980 [DE] Fed. Rep. of Germany ....... 3028791

[51] Int. Cl.³ ................ C07D 211/72; C07D 211/84; C07D 213/56
[52] U.S. Cl. ..................................................... 546/316
[58] Field of Search ......................................... 546/316

[56] References Cited

U.S. PATENT DOCUMENTS

| | | | |
|---|---|---|---|
| 2,412,749 | 12/1946 | Pike | 546/316 |
| 2,471,518 | 5/1949 | Duesel | 546/316 |
| 2,483,250 | 9/1949 | Suter | 546/316 |
| 3,678,060 | 7/1972 | Finkelstein | 546/316 |

FOREIGN PATENT DOCUMENTS

| | | | |
|---|---|---|---|
| 87228 | 7/1959 | Denmark | 546/316 |
| 828247 | 7/1953 | Fed. Rep. of Germany | 546/316 |
| 2517054 | 10/1976 | Fed. Rep. of Germany | 546/316 |
| 879551 | 10/1961 | United Kingdom | 546/316 |
| 170509 | 4/1965 | U.S.S.R. | 546/316 |

OTHER PUBLICATIONS

Krewson, J. Amer. Chem. Soc., vol. 65, pp. 2256–2257, (1943).
Galat, J. Amer. Chem. Soc., vol. 70, p. 3945, (1948).

*Primary Examiner*—Henry R. Jiles
*Assistant Examiner*—Robert C. Whittenbaugh
*Attorney, Agent, or Firm*—Cushman, Darby & Cushman

[57] ABSTRACT

Crude nicotinamide is purified by a recrystallization and thereby is particularly freed from nicotinic acid and salts of nicotinic acid. As solvent there is used 2-methylpropanol-1 containing water. The warm solution after dissolving the crude nicotinamide is treated with ion exchangers.

19 Claims, No Drawings

PROCESS FOR THE PURIFICATION OF NICOTINIC ACID AMIDE

BACKGROUND OF THE INVENTION

The invention is directed to a process for the recovery of pure nicotinamide from crude nicotinamide by recrystallization in alkanol. The invention particularly is directed to a process for freeing the nicotinamide from the impurities nicotinic acid and salts of nicotinic acid, e.g. sodium nicotinate, ammonium nicotinate and potassium nicotinate.

Nicotinamide is generally produced by hydrolysis of nicotinonitrile in acid or alkaline medium or by reaction of nicotinic acid with ammonia. The crude nicotinamide obtained in this process of production contains impurities, especially nicotinic acid (generally about 0.3 to 5.0%) and salts of nicotinic acid (generally about 1.5 to 2.5%). These impurities create problems in the further use of the nicotinamide, namely in the pharmaceutical area, especially if their amount exceeds 0.1%.

It is known to purify crude nicotinamide with the help of ion exchangers. The nicotinamide for this purpose is led in solution in water or polar organic solvent, in a given case at an elevated temperature up to 50° C. over an anion exchanger and thereby the nicotinate ions are bound (British Pat. No. 879551 and Finkelstein U.S. Pat. No. 3,678,060. The entire disclosures of the British patent and Finkelstein are hereby incorporated by reference and relied upon). These processes require considerable expense and give poor yields if there should be obtained nicotinamide sufficiently purified from nicotinate ions. Besides they are only suited for the cases where there is not needed a separation of the cations.

It is also known to purify crude nicotinamide by recrystallization. In this case there are used as solvents acetone (Duesel, U.S. Pat. No. 2,471,518), propanol-2 or butyl acetate in the presence of decolorizing carbon (German Pat. No. 828,247), ethyl acetate (Krewson, J. Amer. Chem. Soc. Vol. 65 pages 2256–2257 (1943)), ethanol in the presence of activated carbon (Galat, J. Amer. Chem. Soc. Vol. 70 page 3945 (1948)), dioxane or petroleum ether (Pike U.S. Pat. No. 2,412,749) or benzene (Danish Pat. No. 87228).

A disadvantage of these processes is that for the production of a sufficiently pure nicotinamide multiple recrystallization is required and only a moderate yield of pure nicotinamide is produced.

SUMMARY OF THE INVENTION

There has now been found a process for the recovery of pure nicotinamide from crude nicotinamide by recrystallization in alkanol which is characterized by the recrystallization being carried out in 2-methylpropanol-1 containing water and after the solution of the crude nicotinamide the warm solution present is treated with ion exchangers. In this process an outstandingly pure nicotinamide is obtained with favorable yield with only a single recrystallization.

The process of the invention is suitable for the purification of crude nicotinamide as it is obtained from the reaction mixture as it occurs in the customary processes for the production of nicotinamide, especially in the hydrolysis of nicotinonitrile in acid or alkaline medium or in the reaction of nicotinic acid with ammonia. With advantage there is used the process for the purification of the nicotinamide produced by the process of German OS No. 2,517,054. The entire disclosure of German OS No. 2,517,054 is hereby incorporated by reference and relied upon.

According to the invention there is used as the solvent for the recrystallization 2-methylpropanol-1 which contains water. Suitably the 2-methylpropanol-1 contains 1 to 18 weight percent water. Preferably there is employed 2-methylpropanol-1 containing 10 to 18 weight percent water, especially 2-methylpropanol-1 saturated with water.

To carry out the process of the invention the crude nicotinamide was dissolved in the solvent with heating. For the dissolution of the nicotinamide with advantage there is chiosen a temperature from above 50° C. to nearly the boiling point of the solution, preferably a temperature of about 60° to 100° C., especially from 65° to 85° C. Suitably there is prepared a solution which is substantially saturated to the maximum extent possible at the temperature employed.

According to the invention the warm solution is heated with ion exchangers, namely according to the type of impurities to be eliminated with a cation exchanger (e.g. a sulfonated styrene-divinyl benzene copolymer) or an anion exchanger (e.g. a moderately strongly basic styrene-divinyl benzene copolymer tertiary amine resin) or successively in any sequence with a cation exchanger and an anion exchanger. As cation exchangers there is employed commercial acid, preferably a strongly acid, ion exchanger, for example based on polystyrene or styrene-divinyl benzene copolymer, especially such containing free sulfonic acid groups and as anion exchangers there is employed a commercial basic, preferably weakly to moderately strongly basic ion exchanger, for example based on polystyrene or styrene-divinyl benzene copolymer having a macroporous structure, especially such a polymer having amino groups which are exchange active. Some useful ion exchange resins are mentioned in Finkelstein U.S. Pat. No. 3,678,060. The treatment of the nicotinamide solution with the ion exchanger takes place in any customary manner for carrying out ion exchange processes. The amount of ion exchanger to use depends on the amount of impurities which should be eliminated and the desired purity of the solution.

After the treatment with the ion exchangers the solution is cooled off and the pure nicotinamide separated off. The mother liquor can be used directly for a further batch.

Unless otherwise indicated all parts and percentages are by weight.

The process can comprise, consist essentially of or consist of the stated steps with the material set forth.

DETAILED DESCRIPTION

Example 1

There were mixed 2500 grams of crude nicotinamide which contained 2.3% sodium nicotinate and 0.8% nicotinic acid with 2100 grams of 2-methylpropanol-1 and 400 grams of water. The mixture was heated under reflux and thereby the nicotinamide dissolved. The solution was then cooled to 70° C. and while maintaining this temperature was led successively over columns of a strongly acid cation exchanger and a moderately strong basic anion exchanger. The throughput velocity was 5 liters of solution per liter of exchanger per hour. The cation exchanger was Lewatit S 100 (exchanger based on polystyrene having sulfonated groups). It was used up to a capacity of 1.62 val per liter of exchanger and resulted in a lowering of the sodium ion content in the solution to below 1 ppm, based on the content of nicotinamide in the solution. The anion exchanger was Lewatit MP 64 (exchanger based on polystyrene having amino groups). It was used to a capacity of 0.38 val per liter of ion exchanger and caused the content of nicotinate ions to be reduced to below 0.02%, based on the nicotinamide in the solution. Then there was led over the ion exchanger for rinsing 250 grams of 2-methylpropanol-1 which contained 16% water and had been heated to 70° C. The rinsing liquid was combined with the remaining nicotinamide solution and this was then slowly cooled to 10° C. The nicotinamide crystallized out was filtered off with suction, washed three times, each time with 150 ml of anhydrous 2-methylpropanol-1 and dried. The yield was 1760 grams, corresponding to 73%, based on the nicotinamide employed with raw material. Nicotinic acid was not detectable in the nicotinamide recovered. The sodium content was below 0.001%. The mother liquor remaining after the separation of the nicotinamide was used directly for further batches. For the use in these batches the cation exchanger was regenerated by treatment with dilute aqueous hydrochloric acid and the anion exchanger regenerated by treatment with dilute aqueous sodium hydroxide solution. In these batches the yield of nicotinamide was 96%, based on the nicotinamide employed with the crude material. The nicotinamide even after 10 batches showed the same purity as the product recovered in the first batch.

The entire disclosure of German priority application No. P 36 28791.3 is hereby incorporated by reference.

What is claimed is:

1. In a process for the recovery of pure nicotinamide from a crude nicotinamide by recrystallization in an alkanol the improvement comprising using 2-methylpropanol-1 containing water as the solvent and treating the warm solution present after dissolving the nicotinamide with an ion exchanger.

2. The process of claim 1 wherein the 2-methylpropanol-1 is saturated with water.

3. The process of claim 1 wherein the 2-methylpropanol-1 contains 1 to 18% water.

4. The process of claim 3 wherein the 2-methylpropanol-1 contains 10 to 18% water.

5. The process of claim 3 wherein the crude nicotinamide contains (1) 0.3 to 5.0% of nicotinic acid or (2) 1.5 to 2.5% of a salt of nicotinic acid or a mixture of (1) and (2) and the content of nicotinic acid and the salt of nicotinic acid is reduced to an amount of not over 0.1% in a single recrystallization.

6. The process of claim 1 wherein the 2-methylpropanol-1 contains 10 to 18% water.

7. The process of claim 6 wherein the crude nicotinamide contains nicotinic acid and sodium nicotinate.

8. The process of claim 5 wherein the salt is the sodium salt or the ammonium salt.

9. The process of claim 1 wherein the solution is treated with the ion exchange resin at a temperature of about 60° to 100° C.

10. The process of claim 5 wherein the solution is treated with the ion exchange resin at a temperature of about 60° to 100° C.

11. The process of claim 4 wherein the solution is treated with the ion exchange resin at a temperature of about 60° to 100° C.

12. The process of claim 3 wherein the solution is treated with ion exchange resin at a temperature of about 60° to 100° C.

13. The process of claim 3 wherein the warm solution has a temperature of from above 50° C. to the boiling point.

14. The process of claim 13 wherein the warm solution has a temperature of 65° to 85° C.

15. The process of claim 13 wherein there is employed successively both a cation exchange resin and an anion exchange resin.

16. The process of claim 13 wherein there is employed a cation exchange resin.

17. The process of claim 13 wherein there is employed an anion exchange resin.

18. The process of claim 5 wherein the content of nicotinic acid and the salt of nicotinic acid is reduced to not over 0.001%.

19. A process according to claim 1 including the step of recycling the mother liquor after separation of the nicotinamide.

* * * * *